(12) United States Patent  
Dick et al.

(10) Patent No.: US 8,029,136 B2  
(45) Date of Patent: *Oct. 4, 2011

(54) METHOD AND DEVICE FOR PERFORMING ONLINE ABERROMETRY IN REFRACTIVE EYE CORRECTION

(75) Inventors: Manfred Dick, Gefell (DE); Eckhard Schroeder, Eckental (DE); Joachim Fiedler, Crailsheim (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/732,476

(22) Filed: Mar. 26, 2010

(65) Prior Publication Data

US 2010/0274233 A1 Oct. 28, 2010

Related U.S. Application Data

(63) Continuation of application No. 11/019,964, filed on Dec. 22, 2004, now Pat. No. 7,699,467, which is a continuation of application No. 09/807,227, filed as application No. PCT/EP00/07821 on Aug. 11, 2000, now Pat. No. 6,848,790.

(30) Foreign Application Priority Data

Aug. 11, 1999 (DE) .................................. 199 38 203

(51) Int. Cl.  
*A61B 3/10* (2006.01)

(52) U.S. Cl. ...................................................... 351/205

(58) Field of Classification Search .................. 351/205  
See application file for complete search history.

(56) References Cited

U.S. PATENT DOCUMENTS

| | | | |
|---|---|---|---|
| 5,062,702 A | 11/1991 | Bille | |
| 5,152,788 A | 10/1992 | Isaacson et al. | |
| 5,493,391 A | 2/1996 | Neal et al. | 356/121 |
| 5,571,107 A | 11/1996 | Shaibani et al. | |
| 5,629,765 A | 5/1997 | Schmutz | 356/121 |
| 5,777,719 A | 7/1998 | Williams et al. | 351/212 |
| 5,864,381 A | 1/1999 | Neal et al. | 351/205 |
| 5,920,373 A | 7/1999 | Bille | 351/212 |
| 5,929,970 A | 7/1999 | Mihashi | 351/205 |
| 5,936,720 A | 8/1999 | Neal et al. | 356/121 |
| 5,949,521 A | 9/1999 | Williams et al. | 351/246 |
| 6,007,204 A | 12/1999 | Fahrenkrug et al. | 351/221 |
| 6,042,233 A | 3/2000 | Mihashi et al. | 351/221 |
| 6,050,687 A | 4/2000 | Bille et al. | |

(Continued)

FOREIGN PATENT DOCUMENTS

DE      19727573      5/1998

(Continued)

OTHER PUBLICATIONS

Klein, A. Stanley, Optimal corneal ablation for eyes with arbitrary Hartmann Shack aberrations, J. Opt. Soc. Am., vol. 15, No. 9, Sep. 1998, pp. 2580 2588.

(Continued)

*Primary Examiner* — George Manuel  
(74) *Attorney, Agent, or Firm* — Leydig, Voit & Mayer, Ltd.

(57) ABSTRACT

A device for correcting visual defects of an eye comprises a coherent light source, a beam modification device for shaping and deflecting a beam of the coherent light source, and a wavefront analyzer device for analyzing a wavefront of an optical path in the eye.

10 Claims, 3 Drawing Sheets

U.S. PATENT DOCUMENTS

| | | | |
|---|---|---|---|
| 6,052,180 A | 4/2000 | Neal et al. ............... | 356/121 |
| 6,086,204 A | 7/2000 | Magnante | |
| 6,095,651 A | 8/2000 | Williams et al. ............ | 351/246 |
| 6,110,166 A | 8/2000 | Juhasz | |
| 6,129,722 A | 10/2000 | Ruiz | |
| 6,130,419 A | 10/2000 | Neal ............. | 250/201.9 |
| 6,155,684 A | 12/2000 | Bille et al. | |
| 6,184,974 B1 | 2/2001 | Neal et al. ............... | 356/121 |
| 6,186,628 B1 | 2/2001 | Van de Velde | |
| 6,199,986 B1 | 3/2001 | Williams et al. ............ | 351/221 |
| 6,220,707 B1 | 4/2001 | Bille ............. | 351/212 |
| 6,234,631 B1 | 5/2001 | Sarver et al. ............... | 351/212 |
| 6,241,356 B1 | 6/2001 | Von Wallfeld | |
| 6,264,328 B1 | 7/2001 | Williams et al. ............ | 351/221 |
| 6,270,221 B1 | 8/2001 | Liang et al. ............ | 351/221 |
| 6,271,914 B1 | 8/2001 | Frey et al. | |
| 6,271,915 B1 | 8/2001 | Frey et al. ............ | 356/124 |
| 6,273,566 B1 | 8/2001 | Kobayashi et al. ............ | 351/221 |
| 6,299,309 B1 | 10/2001 | Ruiz | |
| 6,299,311 B1 | 10/2001 | Williams et al. ............ | 351/221 |
| 6,305,802 B1 | 10/2001 | Roffmann et al. ............ | 351/212 |
| 6,338,559 B1 | 1/2002 | Williams et al. ............ | 351/212 |
| 6,376,819 B1 | 4/2002 | Neal et al. ............... | 250/201.9 |
| 6,379,005 B1 | 4/2002 | Williams et al. | |
| 6,382,793 B1 | 5/2002 | Lai et al. ............... | 351/206 |
| 6,382,795 B1 | 5/2002 | Lai ............. | 351/212 |
| 6,409,344 B1 | 6/2002 | Hayashi ............. | 351/208 |
| 6,428,168 B2 | 8/2002 | Sarver et al. ............ | 351/212 |
| 6,451,008 B1 | 9/2002 | Frey et al. ............. | 606/10 |
| 6,452,145 B1 | 9/2002 | Graves et al. ............ | 250/201.9 |
| 6,460,997 B1 | 10/2002 | Frey et al. ............. | 351/212 |
| 6,497,483 B2 | 12/2002 | Frey et al. ............. | 351/212 |
| 6,525,883 B2 | 2/2003 | Hirohara et al. ............ | 359/618 |
| 6,530,917 B1 | 3/2003 | Seiler et al. ............. | 606/5 |
| 6,536,900 B2 | 3/2003 | Mihashi et al. ............ | 351/221 |
| 6,540,692 B2 | 4/2003 | Mihashi et al. ............ | 600/558 |
| 6,547,393 B2 | 4/2003 | Ruiz | |
| 6,547,395 B1 | 4/2003 | Neal et al. | |
| 6,565,209 B2 | 5/2003 | Campin ............. | 351/212 |
| 6,565,210 B2 | 5/2003 | Kobayashi et al. ............ | 351/214 |
| 6,569,154 B2 | 5/2003 | Campin et al. ............... | 606/5 |
| 6,578,963 B2 | 6/2003 | Pettit ............. | 351/212 |
| 6,585,375 B2 | 7/2003 | Donitzky et al. | |
| 6,598,973 B2 | 7/2003 | Campin ............. | 351/221 |
| 6,629,761 B1 | 10/2003 | Hirohara et al. ............ | 351/221 |
| 6,717,661 B1 | 4/2004 | Bernstein et al. ............ | 356/121 |
| 6,722,767 B2 | 4/2004 | Dick et al. ............. | 351/211 |
| 6,733,132 B2 | 5/2004 | Shevlin ............. | 351/243 |
| 6,750,957 B1 | 6/2004 | Levecq et al. ............... | 356/121 |
| 6,755,818 B2 | 6/2004 | Shimmick et al. ............... | 606/5 |
| 6,755,819 B1 | 6/2004 | Waelti ............... | 606/5 |
| 2001/0041884 A1 | 11/2001 | Frey et al. ............. | 606/5 |
| 2002/0013576 A1 | 1/2002 | Gray et al. ............. | 606/5 |
| 2002/0016629 A1 | 2/2002 | Sandstedt et al. ............ | 623/6.11 |
| 2002/0041359 A1 | 4/2002 | Mihashi et al. ............ | 351/221 |
| 2002/0097376 A1 | 7/2002 | Applegate et al. ............ | 351/205 |
| 2003/0025874 A1 | 2/2003 | Williams et al. ............ | 351/200 |
| 2003/0086063 A1 | 5/2003 | Williams et al. ............ | 351/221 |
| 2004/0059321 A1 | 3/2004 | Knopp et al. ............... | 606/10 |
| 2004/0059398 A1 | 3/2004 | Yee et al. ............. | 607/89 |
| 2004/0060903 A1 | 4/2004 | Neal et al. ............... | 216/41 |
| 2004/0088050 A1 | 5/2004 | Norrby et al. ............... | 623/6.11 |
| 2004/0130677 A1 | 7/2004 | Liang et al. ............... | 351/205 |
| 2008/0251955 A1 | 10/2008 | Williams et al. | |
| 2008/0259273 A1 | 10/2008 | Williams et al. | |
| 2008/0316429 A1 | 12/2008 | Williams et al. | |
| 2009/0002628 A1 | 1/2009 | Williams et al. | |

FOREIGN PATENT DOCUMENTS

| | | |
|---|---|---|
| DE | 19705119 | 8/1998 |
| WO | WO-9201417 | 2/1992 |
| WO | WO 9742891 A1 | 11/1997 |
| WO | 98 27863 | 7/1998 |
| WO | WO 9842291 A2 | 10/1998 |
| WO | WO-9927334 | 6/1999 |
| WO | 00 10448 | 3/2000 |
| WO | 00 45759 | 8/2000 |
| WO | 01 02822 | 1/2001 |
| WO | 01 28410 | 4/2001 |
| WO | 01 28476 | 4/2001 |
| WO | 01 28478 | 4/2001 |
| WO | 01 78584 | 10/2001 |
| WO | 01 82228 | 11/2001 |
| WO | 01 85016 | 11/2001 |
| WO | 01 92838 | 12/2001 |

OTHER PUBLICATIONS

David Stern et al.: "Corneal Ablation by Nanosecond, Picosecond, and Femtosecond Lasers at 532 and 625 nm", Arch. Ophthalmol., vol. 107, Apr. 1989, pp. 587-592.

METHOD AND DEVICE FOR PERFORMING ONLINE ABERROMETRY IN REFRACTIVE EYE CORRECTION

This is a continuation of U.S. application Ser. No. 11,019, 964, filed Dec. 22, 2004, now U.S. Pat. No. 7,699,467 as a continuation of U.S. application Ser. No. 09/807,227, filed Jul. 2, 2001, now U.S. Pat. No. 6,848,790 which is a National Stage entry of PCT/EP00/07821, filed Aug. 11, 2000, which claims priority to German Application No. DE 199 38 203.4, filed Aug. 11, 1999.

The present invention relates to a method and a device for correcting visual defects of the human eye.

BACKGROUND

In ophthalmology, it is known to shape the cornea by ablation of tissue in the case of amblyopia. In this context, the data on the aberration in the optical path of the eye is obtained by questioning the patient about his/her subjective impression of vision on the basis of corrections via standardized corrective lenses in front of the eye of the patient. Besides, methods exist for measuring the outer contour of the eye with the assistance of stripe- or ring-projection systems as are manufactured, for example, by the Orbtek, Tomey, or Technomed companies.

German Patent Application DE 197 05 119 A1 describes a method for improving a Shack-Hartmann sensor which can be used in the field of astronomy to measure wavefronts for surveying stars.

In German Patent 197 27 573 C1, a device and a method for shaping surfaces, in particular of lenses, by laser ablation of the surfaces is specified in a valuable contribution to the technological development.

It is felt to be a disadvantage of the related art that the correction of the lenses takes place only on the basis of suboptimum data on the causes of the visual defects such as irregularities of the cornea surface or aberration in the optical path. Consequently, only corrections according to the standard lens formulas of geometric optics are carried out.

SUMMARY OF THE INVENTION

Therefore, the object of the present invention is to provide a method and a device which permit complete correction of all refractive visual defects, including the aberrations of the optical path in the defective eye.

This objective is achieved by the device and the method according to the independent claims. Advantageous embodiments of the present invention are specified in the subclaims.

In particular, the objective is achieved by a device for correcting visual defects of an eye, including a coherent light source, a beam modification device for shaping and deflecting a beam of the coherent light source, provision being made for a wavefront analyzer device for analyzing a wavefront of the optical path in the eye. This device enables the data obtained from the analysis of the intraocular aberration to be taken into account in the correction of an existing optical system of an eye to be corrected. In this manner, the correction of the optical system of the eye is achievable with added precision.

The considered eye can be, in particular, a human eye but it is also conceivable to correct eyes of other living beings. Visual defects are, in particular, refractive visual defects such as myopia or hyperopia, irregularities of the cornea surface, or aberrations in the optical path.

Provided as coherent light source is preferably a laser, especially preferably a refractive laser, particularly preferably a spot scanning excimer laser. Conceivable is, moreover, a spot scanner using laser light in other ranges of the spectrum, such as a frequency-quintupled YAG laser, an IR laser of around 3 µm such as an Erbium:YAG laser emitting at 2.94 µm or a femtosecond laser (fs Laser).

The beam modification device is preferably composed of a device for shaping a beam and of a device for deflecting and aligning the beam. Preferably used as the device for shaping the beam are lens systems, diffractive structures, and refractive elements. Preferably used as the device for deflecting and aligning the beam are scanner arrangements, prisms, and mirrors.

Preferably usable as wavefront analyzer device is a Shack-Hartmann sensor, which is a sensor that is based on a method for analyzing wavefronts and is used, in particular, in astronomy (see above). Using this wavefront analyzer device, it is possible to measure the whole wavefront emerging from the eye and, in this manner, to acquire data on the visual defects, including the intraocular aberration of the optical path also in the eye.

In a further exemplary embodiment of the present invention, provision is made for a device in which a topography analyzer unit for analyzing the surface of the eye is provided, as well. This analysis provides the data on the curvature and contour possessed by the eye surface, i.e., in particular by the cornea. In this manner, the complete data on the refractive visual defects of the eye is available to the system. Both the possibly not optimum surface contour of the eye, i.e., of the cornea, and the intraocular aberration can now be analyzed and are available to the system in the correction of the optical system of the eye. In this manner, it is possible to completely correct the visual defects of the eye and even to achieve a vision which exceeds that of the normal human eye.

In a further exemplary embodiment of the present invention, provision is made for a device in which, moreover, a control unit for processing signals of the wavefront analyzer unit and/or for processing signals of the topography analyzer unit and/or for controlling the coherent light source and/or for controlling the beam modification device is provided. These control units permit evaluation of the data ascertained by the analyzer units. It is possible for the signals of the wavefront analyzer unit and the signals of the topography analyzer unit to be separately processed and evaluated in the control unit, or to process both data sets in one step. The control unit is preferably composed of several individual control units.

This data is preferably used for providing an ideal optical system. The parameters required for beam modification is determined from this data. These parameters can preferably be used in a further step for controlling the coherent light source, for example, to predetermine amplitude, pulse duration, and energy of the beam. Moreover, these parameters are also preferably used for controlling the beam modification device; here, to predetermine the target spot and the geometry of the beam in the target via the deflection of the beam.

Because of this, it is possible in a preferred exemplary embodiment to calculate, in particular, the shot positions for manufacturing the individual elements.

In a further preferred exemplary embodiment of the present invention, provision is made for a device in which the beam modification device is designed in such a manner that an intraocular lens and/or an eye lens and/or the cornea of the eye and/or a contact lens and/or an implantable contact lens (ICL) and/or a spectacle lens are processable via the beam. The beam, which is preferably controlled by the control unit, now enables an element or workpiece of the lens system to be processed in such a manner that the visual defects or aberration are completely corrected. Such an element is preferably an intraocular lens (IOL) which is prefabricated prior to a corresponding operation. This is particularly preferably an ICL (implantable contact lens) which is placed onto the lens. Based on the entire available data on the visual defects, including the aberration of the eye, this IOL or ICL can be shaped in such a manner that it corrects all existing visual defects. It is also conceivable for the correction to be carried out on the eye lens itself with the assistance of the beam which is preferably controlled by the control unit.

Moreover, it is conceivable to carry out a correction by processing the cornea. It is also preferred to manufacture contact lenses which, in a patient-specific manner, correct all individual defects going beyond the refractive eye defect, such as aberrations, unsymmetrical cylinders, and irregularities of the cornea. Besides, it is also possible to manufacture individual spectacle lenses. Besides excimer spot processing, methods of the optical industry, such as the single point diamond turning method, can also be used for this purpose. In this manner, all elements of the affected optical system can be used for correcting the eye defects.

It is also possible to use a combination of the individual (partly) corrected elements. This is an advantage, in particular if the theoretically possible correction via one element would result in excessive stressing of this element, and if such stressing appears not to be advisable, in particular from the medical point of view.

In a further preferred exemplary embodiment of the device according to the present invention, the control unit is designed in such a manner that the analysis of the optical path in the eye and/or the analysis of the surface of the eye can be carried out virtually simultaneously with the processing of an optical element via the beam of the coherent light source. Due to this modification of the control unit, an "online" test of the optical path in the eye such as it is currently modified via the operation and/or of the surface of this eye at the current point of time can be carried out during the processing of the optical element, i.e., for example during the processing of the cornea via the surgical laser beam, and be taken into account in the further operation or processing. During a laser treatment of the cornea for correcting refractive visual defects of the eye, it is thus possible for the prevailing refractive value of the overall visual apparatus of the eye to be continuously measured and for the sequence of treatment to be exactly adjusted online to the target value of the refraction of the eye in the case that disturbing influences on the treatment are present. This optimized treatment is made possible by this combination of the optical systems of a surgical laser for the ablation of cornea tissue or lens material and of an aberrometer for the analysis of wavefronts or of the surface of the eye. Particularly advantageous in this context is the complete ascertainment of the refractive values (spherocylindrical aberrations and aberrations of higher order) of the whole optical apparatus of the eye which, in the final analysis, are representative of the quality of the attained surgical intervention. By performing the ascertainment completely online and without interrupting the sequence of treatment, provision is made for an optimized device in terms of the time sequence and the attainable precision.

Particularly preferably, it is also possible for the analysis of the optical path or of the surface of the eye to be carried out in alternation with the processing of the optical element, thus ascertaining portion-by-portion the progression of the treatment or of the operation of the optical system, in particular of the cornea. It is also conceivable for the scanning and analysis of the optical path or of the surface of the eye to be time-interleaved with the processing via the surgical laser beam. This permits continuous or virtually continuous measurement combined with real device integration (e.g., every second) and continuous recalculation of the laser control.

Moreover, the objective is achieved by a method according to the present invention for correcting visual defects of an eye, the optical path of the eye being determined via a wavefront analysis, and an ideal lens system being calculated which would result in a correction of the visual defects of the eye. This method is particularly preferably employed using a device according to the present invention. In this method, the intraocular aberration of the optical path is available for calculating the correction of the optical system for conversion into an ideal optical system.

In a further method according to the present invention, it is particularly preferred to analyze the topography of the eye as well. In this method, consequently, additional data on the defective vision of the eye is available, in particular on aberrations, unsymmetrical cylinders, and irregularities of the cornea.

In another preferred method, the ideal optical system is provided on the basis of the data obtained from the wavefront analysis and/or from the topography analysis. For this, it is particular preferred to provide only one element from this optical system. In this manner, the correcting element or the correcting elements is/are manufactured in a further step on the basis of the complete data of the defective vision. This procedure thus leads to the complete correction of the defective vision.

In a further preferred method, shot positions for manufacturing the ideal optical system are calculated using the data obtained from the wavefront analysis and/or from the topography analysis. In this manner, it is advantageously possible to use the laser spot excimer method for manufacturing the individual elements of the optical systems. The shot positions are optimized depending on the materials to be used and considering the time needed for manufacture.

In another method of the present invention, the old optical system of the eye is reshaped into the calculated ideal optical system. To this end, either elements of the old optical system are processed directly or correspondingly corrected elements are manufactured and inserted or old elements are replaced with new elements. This method allows the old (defective) optical system of the eye to be converted into a (new) ideal optical system. It is especially preferred to manufacture a new lens or an ICL according to the spot scanning principle using an excimer laser.

It is particularly preferred in the method according to the present invention to process a contact lens which is already located on the eye of the patient. During measurement, the patient preferably wears already a contact lens correcting standard visual defects or, in the case of emmetropia, only a therapeutic contact lens which especially preferably features good adhesion and constant image characteristics without decentering. Now, the ablation is carried out on the standardized contact lens, thus non-invasively attaining a riskless correction of the higher aberration of the eye. This allows, in particular, higher aberrations to be corrected without risk to the patient and with high treatment safety to enable the optical apparatus of the eye to utilize the resolving power of the retina and to be provided with a super-vision which is superior to that of the normally-seeing eye. Regardless of the characteristics of their own eyes in terms of transmittance values or drying of the tear film, patients can now acquire a preferred super-vision and gain experience therewith in everyday life. The old vision characteristic is restored by removing the contact lens.

For this purpose, it is also preferred to use a therapeutic contact lens without refractive effect. In this connection, all image defects are corrected on this contact lens with the assistance of the laser.

It is particularly preferred to use contact lenses made of PMMA or plastic lenses which, compared to the human cornea, especially preferably feature a small material ablation for the used laser, for example, a 193 nm ArF excimer laser. Particularly preferred are also all soft contact lenses which exhibit nearly the same ablation characteristics as the cornea because of their high water content. Thus, it is possible to determine the exact ablation rates for any standardized-manufacture contact lens material prior to the treatment and, because of this, to carry out a desired refractive correction on the eye in a reproducible manner.

The correction possibility simulated in this manner can serve in a preparatory manner for a later real cornea operation, or such a lens having a customized correction can be used for a predetermined time. In particular in the case of hard contact lenses, longer-term use is also possible. In this context, a corresponding marking for the axial orientation is applied which is paid attention to during insertion.

The optical system preferably includes, as elements, the eye lens and/or an intraocular lens and/or the cornea of the eye and/or a contact lens and/or an ICL and/or at least one spectacle lens. Via refractive surgery, it is possible, for example, for the cornea of the eye to be reshaped so as to correct the existing defective vision (for example, the surface of the cornea via photorefractive keratectomy, PRK, or by ablation of inner tissue layers of the cornea using laser assisted in situ keratomileusis, LASIK). These elements not only feature rotationally geometric corrections but individual structures for correcting the defective vision of the patients. In this manner, it is possible to manufacture intraocular lenses or contact lenses, in particular ICLs which, once they are brought into the lens system, not only roughly correct the defective vision of the eye as in known methods heretofore but which additionally correct all irregularities, unsymmetries, and beam distortions, as well. In this manner, it is possible to attain a vision which exceeds that of the normal human eye. Besides, this method makes it possible to manufacture spectacle lenses which likewise correct all irregularities, unsymmetries, and beam distortions of the defective eye or of the old optical system, as well.

Moreover, the objective is achieved by an ideal optical system which is manufactured according to a method according to the present invention and/or using a devices according to the present invention, the optical system including elements made of materials which are suitable for implantation and/or for adhesion and/or for ablation, in particular plastic or glass. By selecting these materials of the lens system according to the present invention, compatibility in using these elements is guaranteed. Such materials are, for example, PMMA, acrylic, silicone, or a combination of these materials.

In a further exemplary embodiment of the present invention, provision is made for an ideal optical system including elements which contain refractive and/or diffractive structures. In known methods heretofore, refractive and/or diffractive structures are only used in beam shaping. A minilens system guides and shapes the entering beam to attain a special beam distribution in the target plane. The use of such refractive and/or diffractive structures on individual elements of an optical system allows visual defects to be selectively corrected in an exceptionally ideal manner. Using these structures, it is thus possible to correct individual, non-steady aberrations but also to give the optical systems characteristics which a normal human eye does not possess.

The objective of the present invention is achieved, moreover, by an element of an (ideal) lens system having refractive and/or diffractive structures. Such elements can include intraocular lenses, modified cornea, contact lenses, ICLs, or spectacle lenses.

BRIEF DESCRIPTION OF THE DRAWINGS

In the following, exemplary embodiments of the present invention and advantageous refinements will be explained in greater detail on the basis of drawings. In this context.

DETAILED DESCRIPTION

Figure 1:
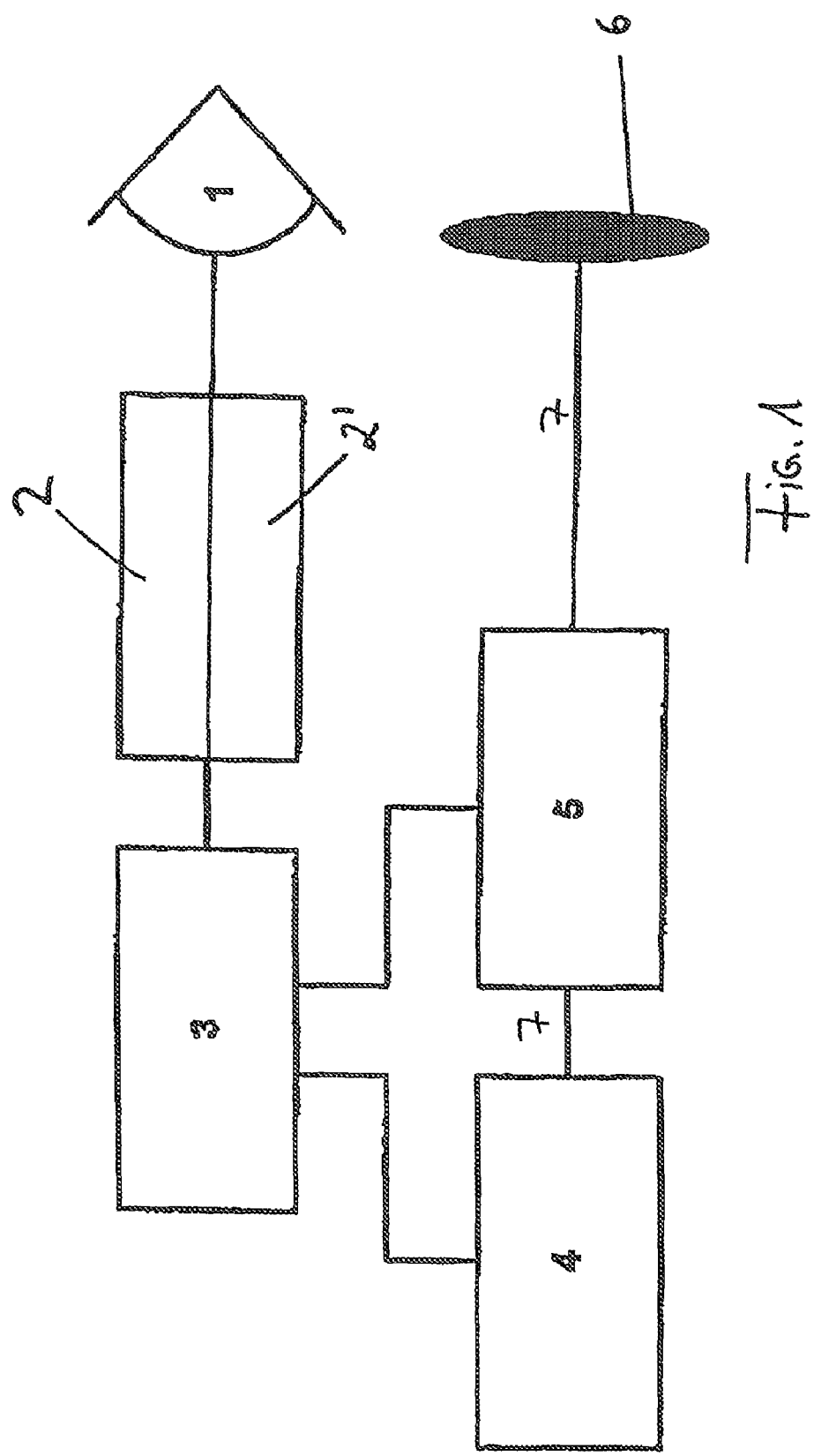
FIG. 1 shows a block diagram for an exemplary embodiment of a device according to the present invention for correcting an aberration in the optical path of an eye on a lens 6.

FIG. 1 depicts a block diagram for an exemplary embodiment of a device according to the present invention for correcting visual defects of an eye on a lens. A wavefront analyzer unit 2 and a topography analyzer unit 2' are connected to a control unit 3. Control unit 3 is connected to a laser 4 and to a beam modification device 5 via a bus. A lens 6 is depicted downstream of beam modification device 5. An eye 1 is shown upstream of wavefront analyzer unit 2 and topography analyzer unit 2'.

In the operating state, the beams of wavefront analyzer unit 2 and topography analyzer unit 2' scan eye 1 and transmit the obtained signals to control unit 3. The beams which are used here are preferably beams of a coherent light source, especially preferably beams of an IR diode or of a green laser. In control unit 3, the signals are processed and the ideal optical system for this eye 1 is calculated. In the depicted case, an ideal lens 6 is calculated here as element of the optical system. In control unit 3, in particular, all shot positions needed for laser 4 to manufacture ideal lens 6 are calculated on the basis of the data obtained from the signals, taking into account the laser-relevant data. Subsequently, control unit 3 triggers laser 4, determining energy and pulse rate of beam 7. Beam 7 is guided through beam modification device 5. In beam modification device 5, beam 7 is shaped and deflected via scanners and lens systems according to the calculated shot positions via the input of control unit 3, so that customer-specific lens 6 is manufactured by ablation of material on the raw lens via controlled surgical laser beam 7. Preferably, control unit 3 can also be designed in several partial control units which can be connected to individual components of the device.

Figure 2:
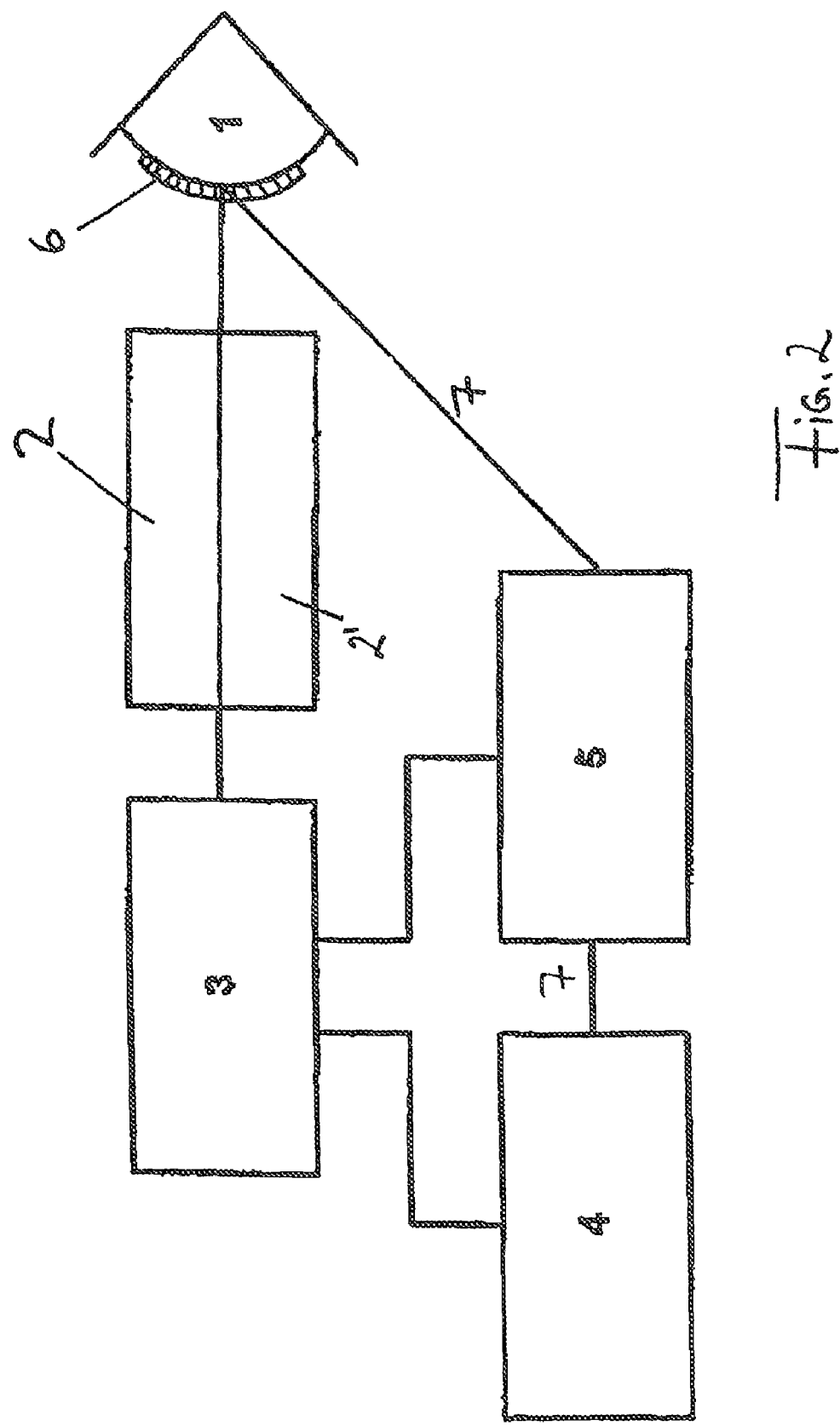
FIG. 2 shows a block diagram for an exemplary embodiment of a device according to the present invention for correcting an aberration in the optical path of an eye to which a lens 6 is applied.

FIG. 2 depicts a block diagram for a further exemplary embodiment of a device according to the present invention for correcting an aberration in the optical path of an eye to which a lens is applied. In principle, the configuration corresponds to that of FIG. 1 with the difference that a contact lens 6 is directly applied to eye 1 and that the ablation is carried out there in situ. To this end, surgical laser beam 7 is directed, preferably via further optical elements such as mirrors (not shown), to lens 6 which rests directly on eye 1. The ablation of the lens material is now carried out in situ on the eye so that the optical path in the system of eye 1 and lens 6 as well as the surface of this system, i.e., here preferably of lens 6, can now be analyzed, preferably online, via analyzer device 2 or 2' concurrently with the ablation, and the treatment via beam 7 can be directly checked and assessed. Ideal lens 6 manufactured in this manner now conveys to the interested person an impression of the complete optical system and of the surgical conditions without having undergone an irreversible operation.

Figure 3:
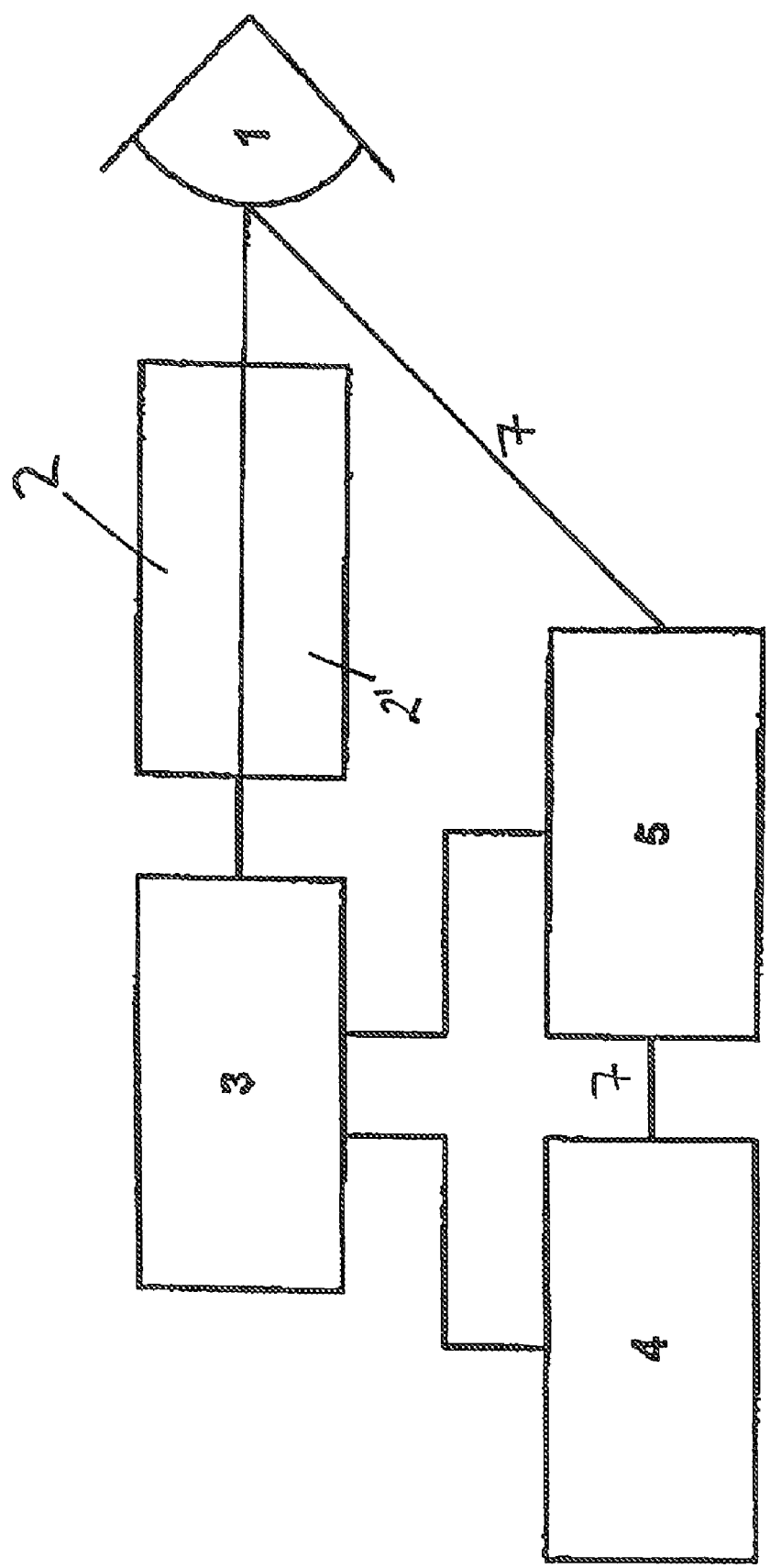
FIG. 3 shows a block diagram for an exemplary embodiment of a device according to the present invention for correcting an aberration in the optical path of an eye on without contact lens.

FIG. 3 depicts a block diagram for an exemplary embodiment of a further device according to the present invention for correcting the aberration in the optical path of an eye without contact lens. Here, preferably simultaneously with the analysis of eye 1 via analyzer device 2, 2', the progression of the operation can be monitored online via the surgical beam 7, and recalculations can be carried out via control unit 3 during the operation so that eye 1 can be treated iteratively via laser beam 7 which reacts and is used in each case as a function of the prevailing conditions. Besides, the progression of the operation can also be monitored visually, for example, via a microscope (not shown).

It is particularly preferred to project a point onto the retina of eye 1 with the assistance of a light source of analyzer device 2, 2' (light source not separately shown). In this context, a nearly parallel external optical path is used, making use of the focusing effect of the optical apparatus of the eye to be able to generate an as small as possible point. In accordance with the used wavelength and the irradiation time, the intensities are so small that no damage can occur on the retina but sufficient reflected intensity exists.

While passing through the aberrative optical system of the eye, the reflective wave detects all image defects. The correspondingly deformed wavefront reaches wavefront analyzer device 2 or topography analyzer device 2' from where the aberration data is preferably fed to a computer via a corresponding electronics or control unit 3. With the assistance of the computer software, a current ablation profile is in each case calculated from the aberration data, the ablation profile triggering excimer laser 4 including the spot scanning system, implementing a target-controlled treatment via beam modification device 5.

Such a measurement can also be carried out sporadically, for example, during 80 percent of the treatment time. Analyzer device 2 or 2' can be arranged on a separate stand so that laser and measuring instrument swing in alternately or, preferably, the measuring instrument is integrated in the laser and measures when the laser bombardment is interrupted. It is particularly preferred for a recalculation of the remaining treatment to be carried out on request of the operator. This measurement can particularly preferably be carried out also continuously or virtually continuously in the case of device integration and continuous recalculation of the laser control.

In this manner, a new and advantageous method and a device for completely correcting visual defects of the human eye have been specified. Combinations of measuring and processing methods have been specified which, when used according to the present invention, enable the human eye to be completely corrected. In doing so, measuring methods are used which can precisely measure the surface of the cornea and which also record the aberrations arising in the further optical path up to the retina. The computer-aided evaluation of these measuring results, in conjunction with the calculation of ideally corrected eye lenses (for example, after cataract operations) or of ideally correcting cornea surfaces, makes it possible to manufacture a patient-specific lens and/or to shape the cornea in an ideally correcting manner, preferably using a spot scanning excimer laser system in a topography-aided manner.

In particular, the correction can be effected via the modification of an element of the optical system. Thus, for improving the vision of a patient having a cataract and a defective vision, it is sufficient to completely correct the intraocular lens. In such a case, it is no longer necessary to carry out a refractive operation in addition to the cataract operation.

LIST OF REFERENCE SYMBOLS

1 Eye
2 Wavefront analyzer device
2' Topography analyzer unit
3 Control unit
4 Coherent light source
5 Beam modification device
6 Optical element/lens

What is claimed is:

1. A device for correcting visual defects of an eye comprising:
   a femtosecond laser configured to generate a pulsed laser beam having femtosecond pulses;
   a beam modification device configured to shape and deflect the pulsed laser so as to process at least one of an intraocular lens and an eye lens;
   a wavefront analyzer device configured to analyze a wavefront of an optical path in the eye and to generate wavefront signals indicative of the wavefront; and
   a control unit configured to process the wavefront signals of the wavefront analyzer device and to control the femtosecond laser and the beam modification device based on the wavefront signals so as to perform a refractive correction.

2. The device as recited in claim 1, wherein the control unit is configured to process the signals simultaneously with the processing of at least one of the intraocular lens and the eye lens.

3. The device as recited in claim 1, wherein the control unit is configured to calculate a plurality of shot positions needed for processing the intraocular lens or eye lens based on the wavefront analysis.

4. The device as recited in claim 1, further comprising a topography analyzer configured to generate topography signals indicative of a topography of the intraocular lens or eye lens and wherein the control unit is configured to process the topography signals and the wavefront signals.

5. The device as recited in claim 4, wherein the beam modification device is configured to process at least one of the intraocular lens and the eye lens so as to form an ideal optical system.

6. A method for correcting visual defects of an eye comprising:
   generating a pulsed laser beam having femtosecond pulses using a femtosecond laser;
   shaping and deflecting the pulsed laser using a beam modification device so as to process at least one of an intraocular lens and an eye lens;
   analyzing a wavefront of an optical path in the eye using a wavefront analyzer device;
   generating wavefront signals indicative of the wavefront;
   processing signals of the wavefront analyzer device using a control unit; and
   controlling the femtosecond laser and the beam modification device using the control unit based on the wavefront signals so as to perform a refractive correction.

7. The method as recited in claim 6, wherein the processing of at least one of the intraocular lens and the eye lens and the processing the signals of the wavefront analyzer are performed simultaneously.

8. The method as recited in claim 6, further comprising calculating a plurality of shot positions needed for processing the intraocular lens or eye lens based on the wavefront analysis.

9. The method as recited in claim 8, further comprising generating topography signals indicative of a topography of the intraocular lens or eye lens using a topography analyzer and processing the topography signals and the wavefront signals using the control unit.

10. The method as recited in claim 9, wherein the processing of at least one of the intraocular lens and the eye lens includes reshaping at least one of the intraocular lens and the eye lens into an ideal optical system.

* * * * *